(12) United States Patent
Siciliano (10) Patent No.: US 12,144,951 B2
(45) Date of Patent: Nov. 19, 2024

(54) GRIP FOR TATTOO, NEEDLING AND PERMANENT MAKEUP MACHINES

(71) Applicant: FK Irons Inc., Doral, FL (US)

(72) Inventor: Gaston Siciliano, Doral, FL (US)

(73) Assignee: FK Irons Inc., Doral, FL (US)

( * ) Notice: Subject to any disclaimer, the term of this patent is extended or adjusted under 35 U.S.C. 154(b) by 606 days.

(21) Appl. No.: 17/354,041

(22) Filed: Jun. 22, 2021

(65) Prior Publication Data

US 2021/0393937 A1 Dec. 23, 2021

Related U.S. Application Data (60) Provisional application No. 63/042,540, filed on Jun. 22, 2020.

(51) Int. Cl.
*A61M 37/00* (2006.01)

(52) U.S. Cl.
CPC . *A61M 37/0076* (2013.01); *A61M 2205/0205* (2013.01); *A61M 2209/08* (2013.01)

(58) Field of Classification Search
CPC .......... A61M 37/0076; A61M 37/0015; A61M 37/0023; A61M 37/0084; A61M 2205/106; A61M 2205/0205; A61M 2209/08

See application file for complete search history.

(56) References Cited

U.S. PATENT DOCUMENTS

| | | | | |
|---|---|---|---|---|
| 4,665,912 | A * | 5/1987 | Burton | A61M 37/0076 606/186 |
| 8,021,357 | B2 * | 9/2011 | Tanaka | A61M 5/14276 604/890.1 |
| 8,435,034 | B2 * | 5/2013 | Gersh | A61C 17/20 433/119 |
| 9,828,789 | B2 * | 11/2017 | Bulancea | E05B 17/002 |
| 9,878,088 | B2 * | 1/2018 | Mellard | A61M 5/1415 |
| 9,974,566 | B2 * | 5/2018 | Scherkowski | A61B 17/3494 |
| 10,201,747 | B2 * | 2/2019 | Mistry | A63F 13/24 |
| 10,226,611 | B1 * | 3/2019 | Collias | F21V 33/00 |
| 10,688,253 | B2 * | 6/2020 | Neumetzler | A61M 37/0076 |
| 10,744,312 | B2 * | 8/2020 | Siciliano | A61M 37/0076 |
| 11,089,660 | B2 * | 8/2021 | Wensley | H05B 1/0244 |
| 11,400,268 | B2 * | 8/2022 | Siciliano | A61M 37/0015 |
| 11,400,425 | B2 * | 8/2022 | Merillat | A61M 37/0084 |

(Continued)

OTHER PUBLICATIONS

Patent Cooperation Treaty, "International Search Report" issued in International Patent Application No. PCT/US21/38381, dated Sep. 29, 2021; document of 10 pages.

*Primary Examiner* — David B. Thomas (74) *Attorney, Agent, or Firm* — Akerman LLP; Peter A. Chiabotti (57) ABSTRACT

A grip apparatus or kit, and methods of use thereof, that includes a grip housing having a cartridge receiving portion and a motor housing mating portion at opposite ends. The cartridge receiving end having dimensioned to receive a needle cartridge. The opposite end dimensioned to receive a motor drive pin of a needling device. The grip apparatus including a resilient barrier within the grip housing, positioned between the cartridge receiving portion and the motor housing mating portion. The resilient barrier comprising a flexible portion that may include alignment structures having concave, convex, stepped configurations, or a combination thereof.

13 Claims, 7 Drawing Sheets

(56) References Cited

U.S. PATENT DOCUMENTS

| | | |
|---|---|---|
| 2012/0271335 A1 | 10/2012 | Lee |
| 2015/0359559 A1 | 12/2015 | Scherkowski |
| 2016/0184572 A1* | 6/2016 | Xiao ................. A61M 37/0076 |
| | | 606/186 |
| 2017/0157382 A1 | 6/2017 | Siciliano |
| 2017/0312399 A1* | 11/2017 | Dehnad ................ A61L 29/148 |
| 2018/0236178 A1* | 8/2018 | Neumetzler ......... A01K 11/005 |
| 2020/0324258 A1* | 10/2020 | Merillat ............ A61M 37/0084 |
| 2021/0244928 A1* | 8/2021 | Siciliano ........... A61M 37/0076 |
| 2021/0353924 A1* | 11/2021 | Zhang ............... A61M 37/0084 |
| 2021/0370035 A1* | 12/2021 | Hill ................... A61M 37/0076 |

* cited by examiner

GRIP FOR TATTOO, NEEDLING AND PERMANENT MAKEUP MACHINES

CROSS REFERENCE TO RELATED APPLICATION

This non-provisional patent application claims priority to, and incorporates herein by reference, U.S. Provisional Patent Application No. 63/042,540 that was filed Jun. 22, 2020.

FIELD OF THE DISCLOSURE

The disclosure relates generally to the field of mechanical apparatuses, and more particularly to tattoo or permanent makeup machine grips, tattoo machine systems with disposable grips, antimicrobial grips, and kits including grips. The disclosed grip can also be useful for tattooing, or for medical-grade services and therapies, such as implantation of temporary or permanent pigments, compounds, chemicals, large molecules and even cells beneath the skin. The disclosure may also be useful for therapeutic microneedling and stimulation.

BACKGROUND

Increasingly, tattoo machines and permanent makeup machines require greater sterility to prevent cross-contamination between clients or patients. Machine grips have become disposable to enhance sterility and reduce cross-contamination. Features of the present disclosure overcome various deficiencies of the prior art by providing a tattoo machine grip having advantages that will become apparent from the following disclosure.

BRIEF SUMMARY OF THE DISCLOSURE

The following presents a simplified summary of the disclosure in order to provide a basic understanding of some aspects of the disclosure. This summary is not an extensive overview of the disclosure. It is intended neither to identify key or critical elements of the disclosure nor to delineate the scope of the disclosure. Its sole purpose is to present some concepts of the disclosure, in accordance with the disclosure, in a simplified form as a prelude to the more detailed description presented later.

Embodiments of the present disclosure may include components manufactured from various materials based upon the contemplated use. By way of example and not limitation, materials may be acrylonitrile butadiene styrene (ABS), thermoplastic elastomer (TPE), or silicone.

The present disclosure may address one or more of the problems and deficiencies of the prior art discussed above. However, it is contemplated that the disclosure may prove useful in addressing other problems and deficiencies in a number of technical areas. Therefore the claimed disclosure should not necessarily be construed as limited to addressing any of the particular problems or deficiencies discussed herein.

The following description and the annexed drawings set forth certain illustrative aspects of the disclosure. These aspects are indicative of only some of the various ways in which the principles of the disclosure may be employed, and the present disclosure is intended to include all such aspects and their equivalents. Other advantages and novel features of the disclosure will become apparent from the following description when considered in conjunction with the drawings.

BRIEF DESCRIPTION OF THE DRAWINGS

The disclosure can be readily understood by considering the following detailed description in conjunction with the accompanying drawings, in which.

DETAILED DESCRIPTION

The following detailed description and the appended drawings describe and illustrate various embodiments of the disclosure solely for the purpose of enabling one of ordinary skill in the relevant art to make and use the disclosure. As such, the detailed description and illustration of these embodiments are purely exemplary in nature and are in no way intended to limit the scope of the disclosure, or its protection, in any manner. It should also be understood that the drawings are not to scale and in certain instances details have been omitted, which are not necessary for an understanding of the present disclosure, such as conventional details of fabrication and assembly.

Figure 1A:
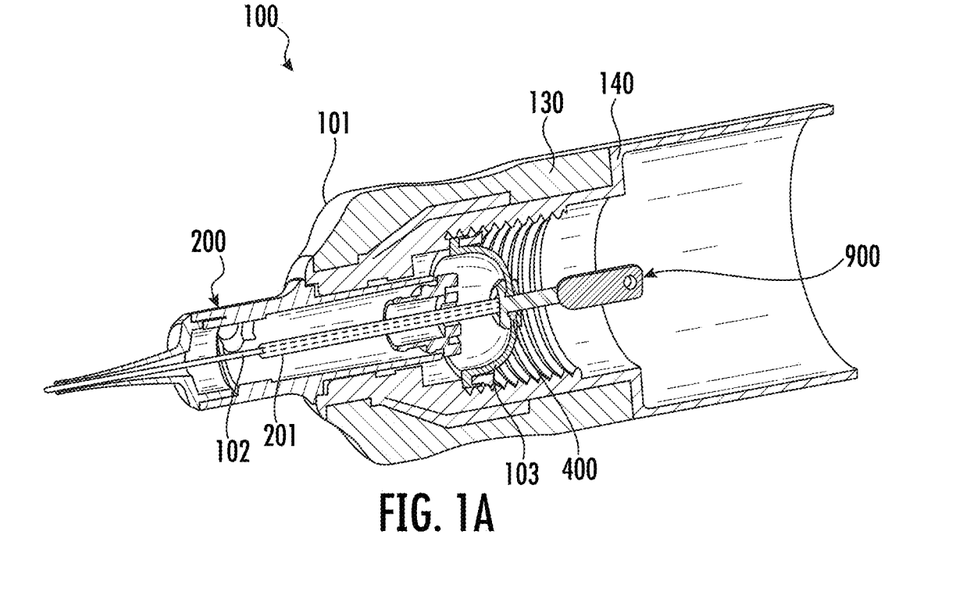
FIG. 1A illustrates a perspective cross-sectional view of an embodiment of a grip in accordance with the disclosure together with needle cartridge inserted in the grip.
Figure 1B:
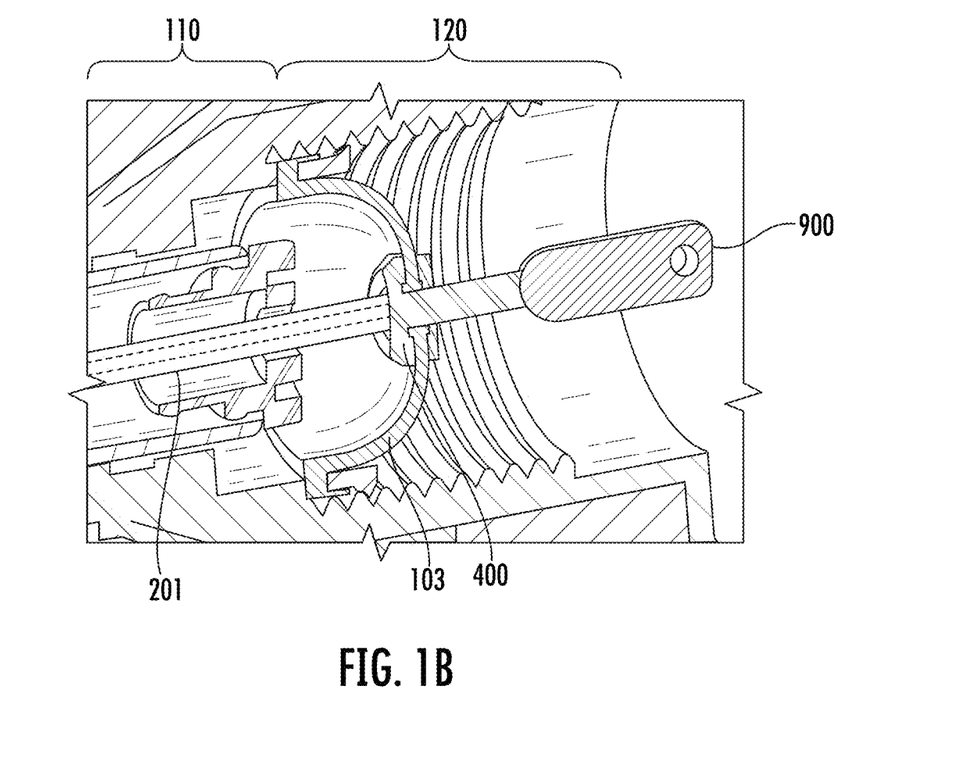
FIG. 1B illustrates a closeup of a perspective cross-sectional view of FIG. 1A, including the barrier components of an embodiment of a grip.

Reference will now be made in detail to the embodiments of the present disclosure, examples of which are illustrated in the accompanying drawings. As shown in FIGS. 1A and 1B, one embodiment of the present disclosure is a tattoo machine grip apparatus 100. The tattoo machine grip apparatus 100 comprises a grip housing 101 with substantially radial symmetry about a central axis, a hollow interior having two openings at opposite ends, a cartridge receiving end/portion 110, and a motor/machine housing mating end/portion 120 distal to the cartridge receiving end 110. The cartridge receiving end 110 has a bore co-axial to the central axis and is dimensioned to receive a back end of a needle cartridge 200 when inserted into a first end of the hollow interior of the grip housing 101. The motor housing mating portion 120 may have a contact disc 400 dimensioned to engage the tip of a motor/machine drive pin 900 when inserted into a second end of the hollow interior of the grip housing 101. The grip housing 101 may include a rigid portion 140 and an overmolded portion 130, which may be made of resilient material providing a soft and ergonomic gripping for the grip apparatus 100. The grip apparatus 100 further comprises a resilient barrier 103 within the hollow interior, positioned between the cartridge receiving end 110 and the motor housing mating portion 120, such that the resilient barrier 103 isolates the cartridge receiving end 110 from the motor housing mating portion 120.

In some embodiments, the grip 100 may also include a contact disc 400 integral with the resilient barrier 103 and where the contact disc 400 is positioned co-axially to the central axis and configured to provide mechanical communication between a machine/motor drive pin 900 and a cartridge pin 201. The cartridge pin 201 may extend from the back end of the needle cartridge 200, and the motor drive pin 900 may extend from the front end of a needling or tattoo machine (not shown). The motor drive pin 900 may be attached and detached from a needling or tattoo machine. In some embodiments, the grip 100 may include a cartridge shaft or pin 201 that couples to the needle 102 on the left side of the cartridge pin 201 and interfaces with the contact disc 400 on the right side of the cartridge pin 201. The cartridge shaft/pin 201 is internal to the needle cartridge 200, and drives the needle 102 in and out of an opening at the tip of the needle cartridge 200.

Figure 2:
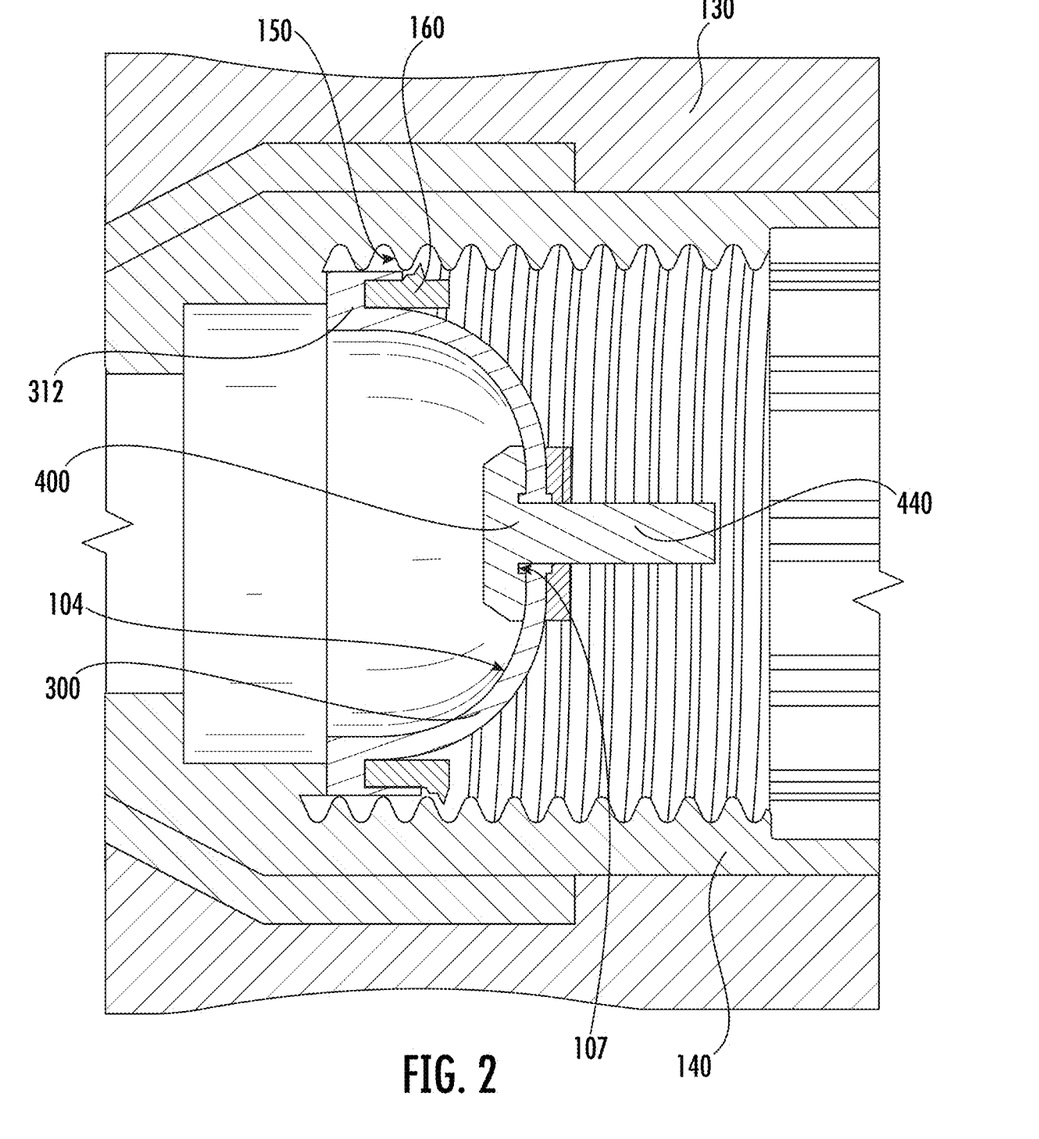
FIG. 2 illustrates a lateral cross sectional view of an embodiment of a grip.
Figure 5:
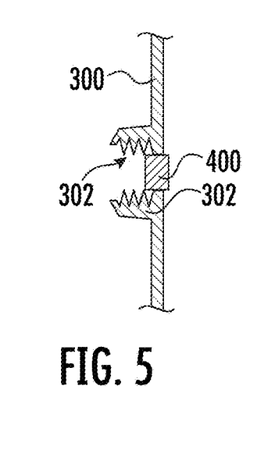
FIG. 5 illustrates a lateral cross sectional view of an embodiment of a grip resilient barrier and disc.

In still other grip embodiments, the resilient barrier 103 may have an outer circumference, the outer circumference co-axial to the central axis and positioned longitudinally distal to the contact disc 400. The resilient barrier 103 may have a deformable concave surface 104, as shown in FIG. 2. The resilient barrier 103 may comprise a flexible portion 300 allowing for repeated deformation. In certain embodiments, the resilient barrier 103 may positioned concentric to the contact disc 400. As shown in FIG. 2, the flexible portion 300 may be positioned concentric to an extended portion 440 of the contact disc 400. In an embodiment, the distal tip of the contact disc 400 may engage the cartridge pin 201 of the needle cartridge 200, where the flexible portion 300 is sealed around the extended portion 440 of the contact disc 400. Further, the resilient barrier 103 may have an outer circumference, a center point, and one or more concentric undulations 302, as shown in FIG. 5, such that the outer circumference is co-axial to the central axis and mated to the hollow interior of the grip 100, the center point is co-axial to the central axis, and the one or more concentric undulations 302 between the outer circumference and the center point.

Referring back to FIG. 2, the grip 100 may further include a retaining ring 160 configured to engage threads 150 on the motor housing mating portion 120. The outer circumference of the flexible portion 300 may comprise a barrier bottom lip 312 that is dimensioned to partially receive the retaining ring 160 such that the retaining ring 160 threadeningly engages the interior threads 150 of the rigid portion 140 of the grip housing 101.

Figure 7A:
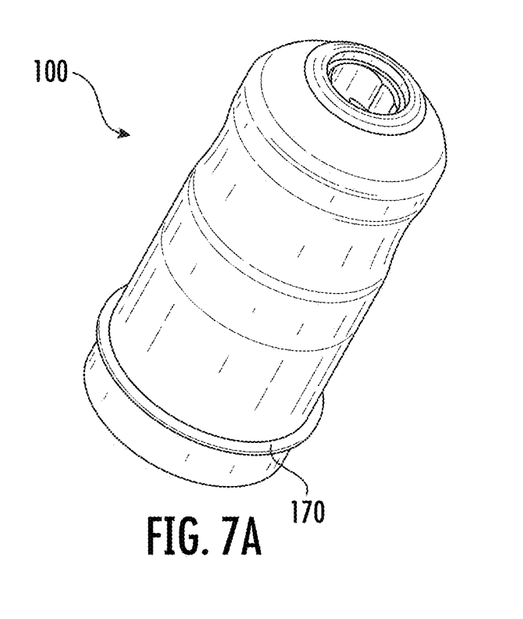
FIG. 7A illustrates a perspective view of an embodiment of a grip.
Figure 7B:
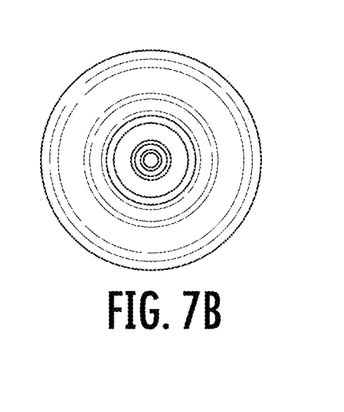
FIG. 7B illustrates a bottom (cartridge tip) plan view of FIG. 7A.
Figure 7C:
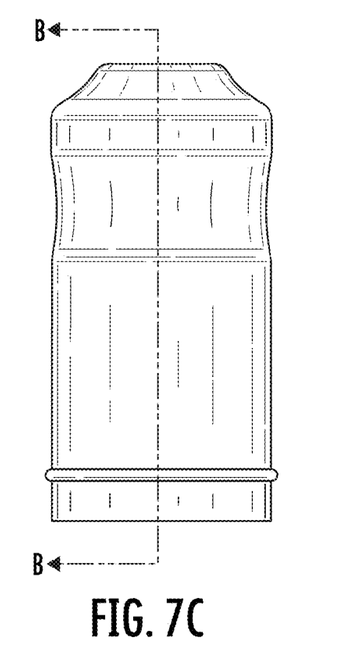
FIG. 7C illustrates a side view of FIG. 7A and showing section B-B.
Figure 7D:
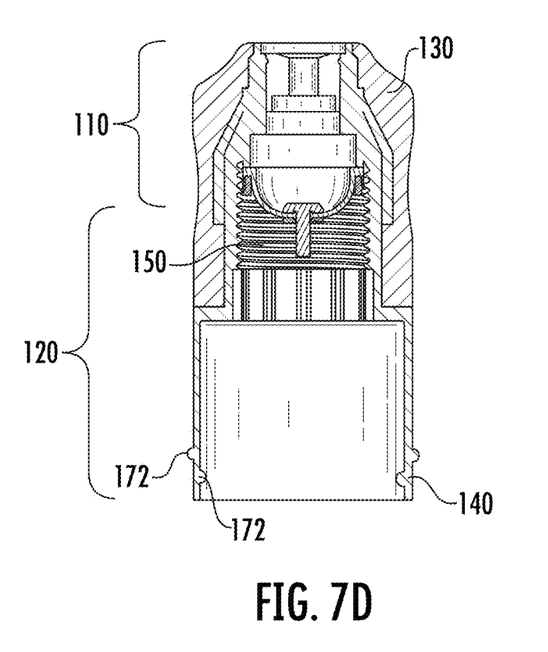
FIG. 7D illustrates a side cross-sectional view section B-B of FIG. 7C.

The motor housing mating portion 120 of the grip housing 101 may include an o-ring or toric joint/gasket 172 on the interior surface of the rigid portion 140 within the motor housing mating portion 120, as shown in FIG. 7D, that is dimensioned to receive the distal tip of a needling machine and provide a tight friction-fit engagement between the grip 100 and the machine. The toric gaskets 172 may isolate and seal the machine drive pin 900 within the interior of the grip 100 from the outside elements, thus preventing contamination from entering into the mechanical components of the machine. Embodiments may include an o-ring or toric joint/gasket 172 positioned within the cartridge receiving end 110 of the grip housing 101 and co-axial to the central axis, such that the toric gasket 172 seals the cartridge receiving end 110 when a needle cartridge 200 is inserted into and constrained within the cartridge receiving end 110.

Referring again to FIG. 2, embodiments may include a circumferential groove 107 on the contact disc 400 which is dimensioned to accept or receive an inner circumference of the resilient barrier 103 such that the contact disc 400, when mated to the resilient barrier 103, forms a seal between them.

Figure 3A:
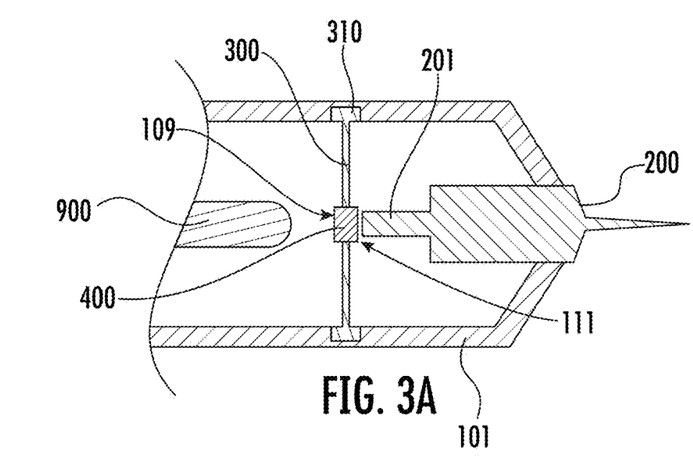
FIGS. 3A and 3B illustrate lateral cross sectional views of other embodiments of a grip.
Figure 9:
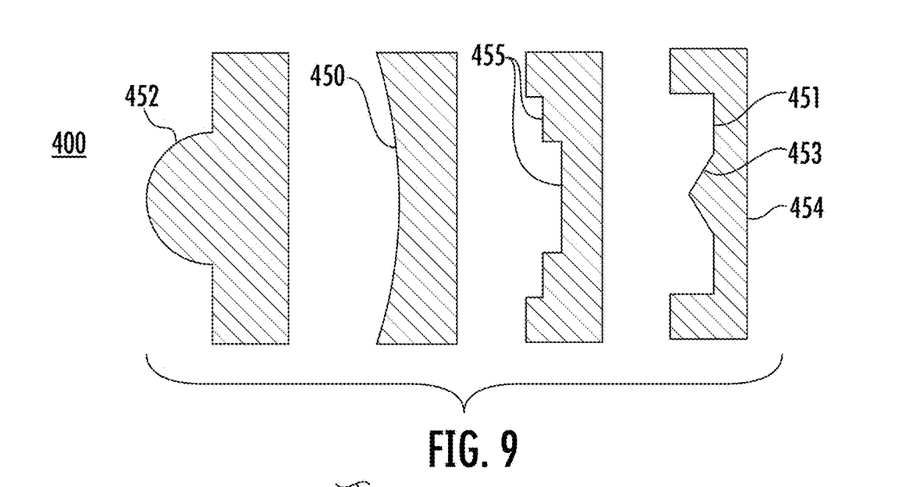
FIG. 9 illustrates lateral cross sectional views of alternative embodiments of centering features on a contact disc as part of a grip.

Alternative embodiments may include alignment features 108 on the contact disc 400. In some embodiments, as shown in FIG. 3A, the grip 100 may include a contact disc 400 without an extended portion 440. The contact disc 400 may have a machine face 109 and a cartridge face 111. The cartridge face 111 may directly engage the cartridge pin 201 of the needle cartridge 200, and may have one or more alignment features 108 as illustrated in FIG. 9. Similarly, the machine face 109 may have one or more alignment features 108. Further, both the cartridge face 111 and the machine face 109 may each have one or more alignment features 108. The alignment features 108 may be concave, stepped, convex, or combination of such features.

Figure 13:
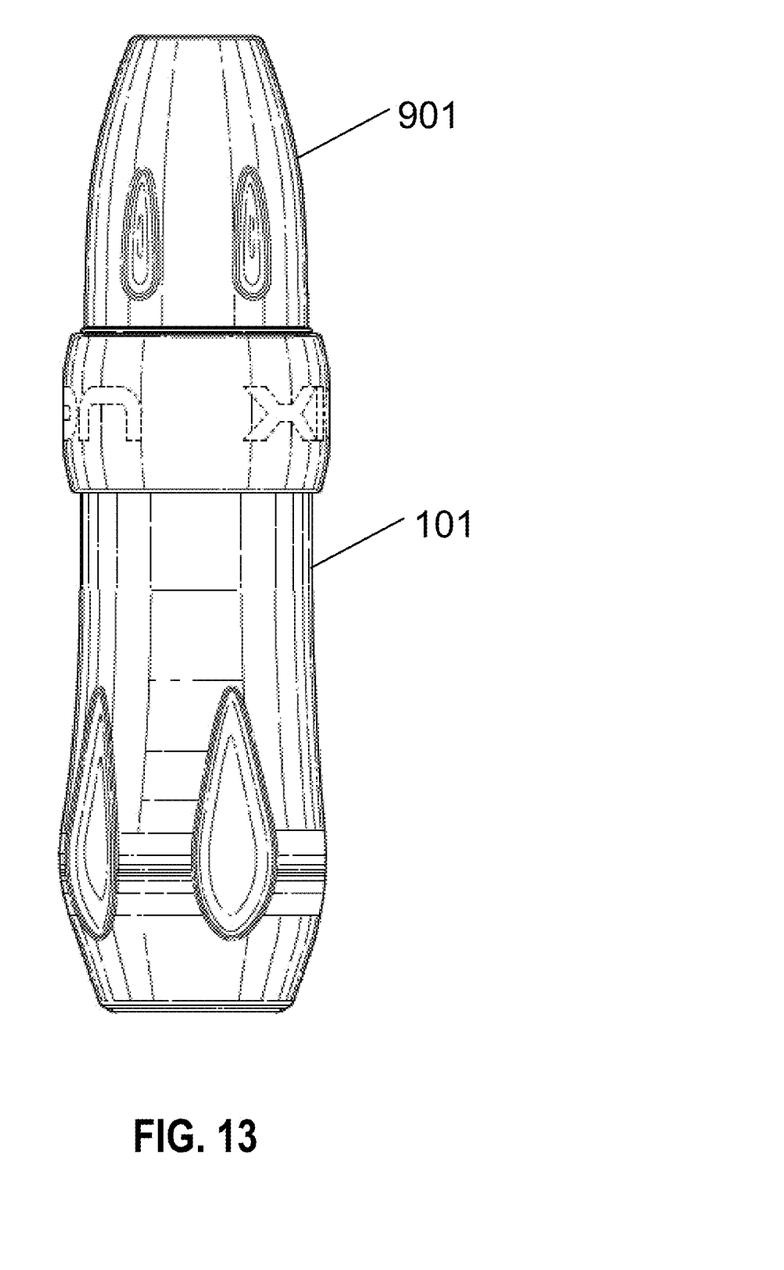
FIG. 13 illustrates a reciprocating or needling machine attached to a grip housing in one embodiment of a grip.

The present disclosure includes a tattoo machine kit 112 including a substantially cylindrical grip housing 101 having a hollow interior with substantially radial symmetry about the outer circumference of the grip housing 101 defining a central axis, and the grip housing 101 also having a cartridge receiving end 110 and a motor housing mating portion 120 distal to and opposite from the cartridge receiving end 110. The cartridge receiving end 110 has a bore co-axial to the central axis and is dimensioned to receive a needle cartridge 200. The grip housing 101 also includes a resilient barrier 103 within its hollow interior, positioned between the cartridge receiving end 110 and the motor housing mating portion 120, such that the resilient barrier 103 isolates the cartridge receiving end 110 from the motor housing mating portion 120. Together with the grip 100 and an inserted needle cartridge 200, the kit 112 includes a machine drive pin 900 for a reciprocating or needling machine. The motor drive pin 900 may be dimensioned for attaching and detaching from the reciprocating machine 901, shown in FIG. 13. The reciprocating machine 901 may enclose a power source, or be operatively connected to a power source. Referring back to FIG. 1A, the motor drive pin 900 may have a hole approximate to one end that is dimensioned to receive a mounting member of the reciprocating machine. The reciprocating machine may be configured to operatively mate with the motor housing mating portion 120 of the grip housing 101. In some embodiments, the kit includes such a reciprocating machine. The motor housing mating portion 120 of the grip housing 101 may include an o-ring or toric joint/gasket 172, as shown in FIG. 7D, that is dimensioned to receive the distal tip of a needling machine that is inserted into the first end of the hollow interior of the grip housing 101 and provide a tight friction-fit engagement between the grip 100 and the machine.

The disclosure also includes a method of using a grip 100, including the step of providing a grip 100 having a cartridge receiving portion 110 and a machine mating portion 120, providing a reciprocating machine configured to operatively mate with the grip 100, connecting the grip 100 to the reciprocating machine, providing a first needle cartridge 200, connecting the needle cartridge 200 to the grip cartridge receiving portion 110, and operating the assembled cartridge-grip-machine.

In other embodiments of a method of using a grip 100 may include providing a second needle cartridge 200, removing the first needle cartridge 200 from the grip cartridge receiving portion 110, operatively mating the second needle cartridge 200 to the grip 100, and operating the assembled cartridge-grip-machine.

The disclosure further includes a tattoo machine grip apparatus 100 having an antimicrobial material or surface, which can include antimicrobial particles embedded in the grip material.

Now, with reference to the resilient barrier 103, it is provided internally within the grip 100, comprising a deformable impermeable barrier 103 between the cartridge receiving end 110 of the grip housing 101 and the machine mating portion 120 of the grip housing 101. The resilient barrier 103 flexes as the machine drive pin 900 actuates, rectilinearly through the resilient barrier 103, the needle cartridge 200. In some embodiments, the resilient barrier 103 is configured to provide minimal resistance to deformation, thus limiting stress on the machine motor and other components. Accordingly, in certain embodiments, the thickness of the resilient barrier 103, according to its material construction, should be sufficiently thin so as to deform with as little force as possible yet maintain resilience and integrity over prolonged periods of use.

In some embodiments, as shown in FIG. 1A, the resilient barrier 103 is configured with a domed shape, having an arctuate curvature when viewed cross-sectionally, and oriented within the grip housing 101 such that its top-center point faces the machine side, while its outer circumference seals against the grip housing 101 is nearer to the cartridge end relative to its top-center point. In such embodiments, the curved portion of the resilient barrier 103 may have uniform or non-uniform thickness along the arc from the bottom lip 312 to the top lip that engages the contact disc 400. The resilient barrier 103 may be configured to minimize the force required to deform the resilient barrier 103 from its resting position to its actuated position. Stated differently, the resilient barrier 103 may not necessarily serve to retract the needle cartridge pin 201 or the motor drive pin 900. In the actuated and extended position of resilient barrier 103, minimal resistive force may be imparted on the machine drive pin 900.

Material used in the resilient barrier 103 may be selected from among those that provide resilient and flexible mechanical properties. Suitable materials may be selected from among acrylonitrile butadiene styrene (ABS), thermoplastic elastomer (TPE), silicone, and other polymers and plastics.

The grip interior seat portion of the grip 100 sealing the machine-facing side of the grip assembly from the cartridge-facing portion of the grip may vary. In one embodiment, the grip interior seat portion may be configured to provide a flat mating surface at a bottom portion of the grip interior corresponding to a flat mating surface on the resilient barrier bottom lip 312, such that the resilient barrier 103 may be inserted into the grip interior, and compressed against the bottom flat mating surface.

In another embodiment, the grip interior seat portion may be configured to provide a circumferential mating surface on an inner perimeter of the grip interior corresponding to a circumferential mating surface on the resilient barrier bottom lip 312. In this configuration, the resilient barrier 103 may be inserted into the grip interior and compressed axially outward, and against the circumferential mating surface of the grip interior, or longitudinally downward along the central axis, and against another mating surface of the grip interior, or both.

Other embodiments of the grip interior mating surface portion may vary such that the resilient barrier bottom lip 312 extends partially rearwardly from the bottom of the resilient barrier 103, forming a groove in which a retaining ring 160 may correspondingly insert.

Still other embodiments of the grip interior seat portion may provide that the resilient barrier bottom lip 312 extends partially forwardly from the bottom of the resilient barrier 103, forming a forward-facing groove in which a portion of the grip interior correspondingly inserts. In this configuration, a threaded retaining ring 160 may compressed the resilient barrier bottom lip portion 312 into and against the corresponding grip interior seat portion.

The resilient barrier 103 may alternatively be manufactured and molded directly into the interior of the grip housing 101, thus obviating the need for a separate retaining ring 160.

Yet another embodiment may provide for a rigid component molded into the resilient barrier 103 itself such that, when inserted into the interior of the grip housing 101, it snaps into place such that the resilient barrier bottom lip 312 seals off the cartridge-facing portion of the grip 100 from the machine-facing portion of the grip 100.

The center of the resilient barrier 103 may include a contact disc 400 providing mechanical communication between and rectilinear translation from the machine drive pin 900 through the resilient barrier 103 to the needle cartridge 200. The contact disc 400 may include features to ensure centering or alignment of the machine drive pin 900 and the cartridge pin 201. Such alignment features 108 may be on one or both sides of the contact disc 400 and may include one or a combination of several alignment features 108.

As shown in FIG. 9, such alignment features 108 may consist of convex or concave configurations. Alternatively, the contact disc 400 may have no alignment features 108, and instead consist of a uniformly flat and parallel surface on each side of the disc 400. As still yet a further alternative, one side of the contact disc 400 may be flat or have no alignment features 108, while the opposite side includes one or more such alignment features 108. The outer perimeter of the contact disc 400 may be round, oval, square, polygonal, or any other regular or irregular geometry.

Alternatively, the resilient barrier 103 may include features integral with the resilient barrier 108 itself to provide greater rigidity (and/or durometer) to ensure sufficient translation of the oscillating drive force from the machine to the needle cartridge 200. Such drive contact area may further include anti-slip coating or material to ensure continuous alignment of the machine drive pin 900 with the cartridge pin 201 during operation. In one such embodiment, a rigid contact disc 400 may be (over) molded directly into and completely covered by the resilient barrier 103.

A further alternative provides no distinct area on the resilient barrier 103 itself, as the machine drive pin 900 and cartridge pin 201 may be sufficiently aligned as a result of the machine's configuration, tolerances, and position within the grip when operatively connected thereto.

In some embodiments, the grip housing 101 may include an o-ring or toric gasket 172 positioned within or at the tip of the cartridge receiving end 110, thus providing a seal between the grip 100 and cartridge 200 when the cartridge 200 is operatively inserted into and engaged with the grip 100. Similarly, the machine mating portion of the grip 100 may include an o-ring or toric gasket 172, or features to accept or receive an o-ring or toric gasket 172 mounted to the machine. The machine o-rings or toric gaskets 172 may further serve to isolate and seal the machine drive pin 900 within the grip interior from the outside elements, thus preventing contamination from entering into the mechanical components of the machine.

The grip 100 may also include features to equalize pressure between the machine-side and the cartridge-side of the resilient barrier 103.

In one embodiment, the grip 100 may have a cooperative pressure-equalizing system integral with the grip body. One or more valves may be situated within the interior of the grip housing 101.

The grip 100 or the exterior material or surface of the grip 100 may also be manufactured of a polymer mixture having antimicrobial additives or particles. Such additives or particles may include silver or silver ions. The silver or silver ions may be distributed evenly within the polymer mixture, or may be particle-based. Silver particles may be impregnated within the polymer throughout, or applied as a coating to the exterior of the grip housing 100.

With reference again to FIGS. 1A and 1B, an embodiment of the tattoo machine grip 100 is provided in accordance with the disclosure. The grip 100 is configured to accept a needle cartridge 200 and to provide isolated mechanical communication from machine/motor drive pin 900 to the needle cartridge 200.

FIG. 2 illustrates an embodiment of the tattoo machine grip partially shown in lateral cross sectional view. The resilient barrier 103 includes a flexible portion 300 allowing for repeated deformation as the tattoo machine drive pin 900 (not shown) drives the contact disc 400 via an extended portion 440. At the outer circumference of the resilient barrier 103 is a barrier bottom lip 312 dimension to partially accept retaining ring 160 such that the retaining ring threadeningly engages interior threads on the grip housing 101, and thereby forms a seal at the bottom lip 312. In some embodiments, the overmolded portion 130 surrounds the rigid portions 140.

Figure 3B:
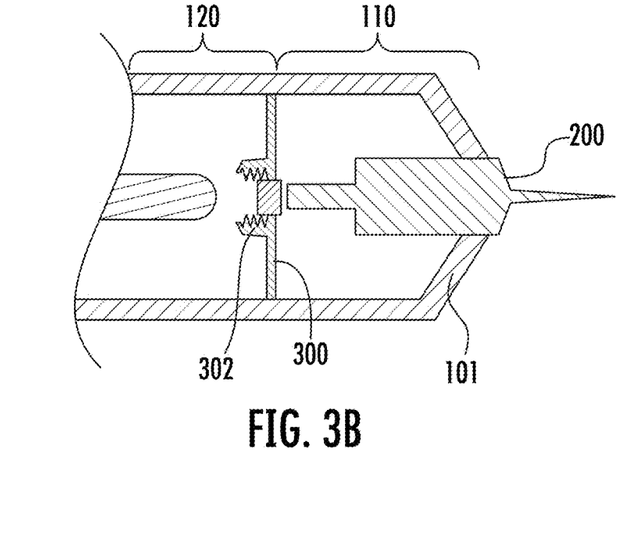

With regard to FIGS. 3A and 3B, alternative embodiments of a tattoo machine grip 100 are provided, illustrated by a lateral cross sectional view showing an alternative isolation of the cartridge receiving portion 110 from the machine mating portion 120. Such isolation can be accomplished by a barrier-grip mating portion 310 contained within the interior of the grip 100. Alternatively, the resilient barrier 103 may be attached to the interior surface of the grip housing 101, as shown in FIG. 3B. In some embodiments, the resilient barrier 103 may be overmolded from the grip housing 101 and integral with the grip housing 101 itself. These alternative configurations of the resilient barrier 103 maintain isolation between the needle cartridge 200 and the machine drive pin 900. In certain embodiments, when the grip 100 is assembled to a machine, the machine mating portion 120 is thereby isolated from both the exterior of the combined machine-grip-cartridge, and the internal cartridge receiving portion 110. In some embodiments, the resilient barrier 103 may be orthogonal to the side wall of the grip housing interior.

Figure 4:
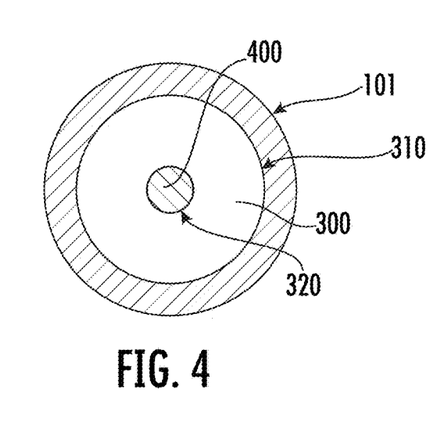
FIG. 4 illustrates a top view of a grip.

FIG. 4 illustrates a top view of an embodiment of a tattoo machine grip 100 in which the flexible portion 300 of the resilient barrier 103 includes a barrier disc mating portion 320, providing a seal between the flexible portion 300 and the grip housing 101. Similarly, the resilient barrier 103 includes a barrier-grip mating portion 310, providing a seal between the resilient barrier 300 and the grip housing 100.

Turning to FIG. 5, a portion of an embodiment of the flexible portion 300 of the resilient barrier 103 engaged with a contact disc 400 is shown in lateral cross sectional view. The barrier 103 includes a flexible or deformable portion 300, and may include one or more undulations 302 between the contact disc 400 and the outer circumference of the resilient barrier 103. Multiple configurations of the flexible portion of the resilient barrier 103 are contemplated by the disclosure.

Figure 6:
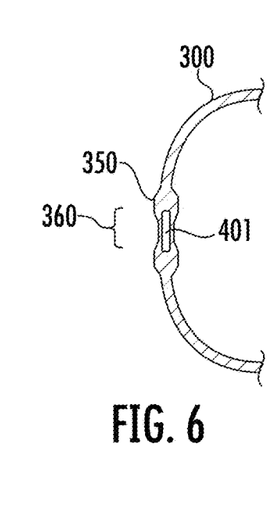
FIG. 6 illustrates a lateral cross sectional view of an embodiment of a grip showing an embedded contact disc within the resilient barrier.

FIG. 6 illustrates still yet a further alternative of a resilient barrier 103 in lateral cross sectional view in which an embedded contact disc 401 exists within the material provided for with the barrier flexible portion 300. In this embodiment, the area providing mechanical communication from the machine drive pin 900 to the needle cartridge 200 may further include alignment features 350, such as a concave surface, directly molded into the resilient barrier 103 itself. In this way, contact area 360 is defined by alignment features 350.

With reference to FIGS. 7A, 7B, 7C, and 7D, a further alternative embodiment of a tattoo machine grip 100 is illustrated. FIG. 7A shows a perspective view of a grip 100. FIG. 7B shows a cartridge-end view of a grip. FIG. 7C shows a lateral view of a grip 100, including Section B-B. FIG. 7D shows the lateral cross sectional view of Section B-B in which the grip 100 includes a rigid portion 140, and an overmolded portion 130. The overmolded portion 130 may be of resilient material providing a soft and ergonomic gripping of the grip-machine-cartridge combination. The overmolded portion 130 may comprise an exterior antimicrobial surface, or may be coated with a material having antimicrobial additives or particles. Threads 150 internal to the grip 100 may be provided to operatively interact with corresponding threaded portion of a tattoo machine. As a consequence of the resilient barrier 103, the cartridge receiving portion 110 is isolated from the machine mating portion 120.

Figure 8:
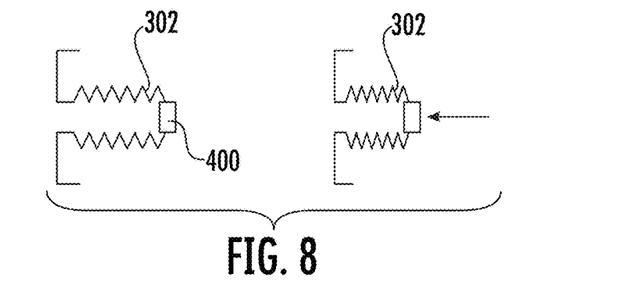
FIG. 8 illustrates compression of the resilient barrier of an embodiment of a grip by the application of force applied from a motor/machine drive pin (drive pin not shown).

FIG. 8 illustrates the operation of one embodiment of a tattoo machine grip resilient barrier 103 in which barrier undulations 302, which form an according structure, collapse upon the application of force applied to contact disc 400. The barrier undulations 302 can be biased in the direction opposite the force of applied by the needle drive to return the grip resilient barrier 103 to an uncompressed position.

Now, with regard to FIG. 9, various embodiments of alignment features of contact disc 400 are illustrated in lateral cross sectional view. The contact disc 400 may include a convex alignment feature 452, a concave alignment feature 450, one or more stepped alignment features 455, an extended alignment feature 453, a recessed alignment feature 451, a combination of any alignment features 108, or without alignment features 108 and providing a flat surface 454 on the contact disc 400.

Figure 10:
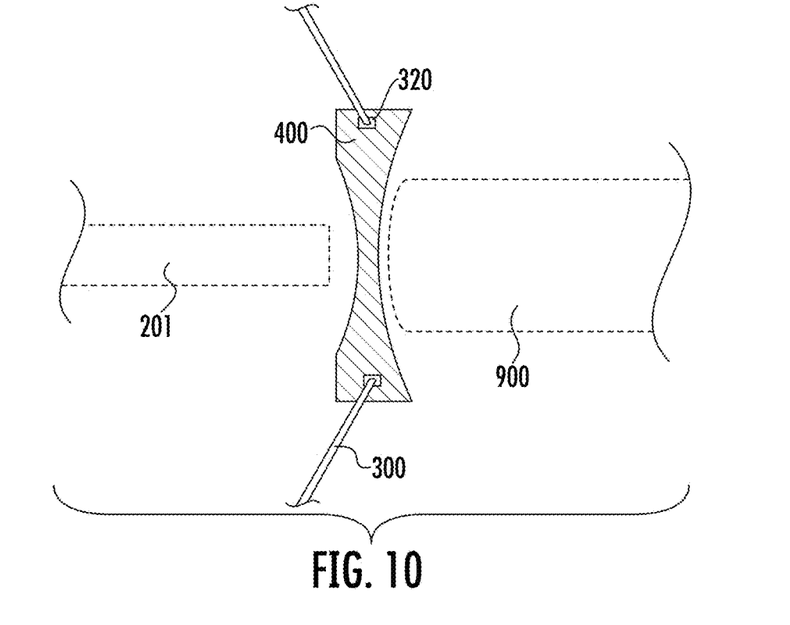
FIG. 10 illustrates a lateral cross sectional view of a resilient barrier and contact disc in an embodiment of a grip.

Turning to FIG. 10, a lateral cross sectional view of a portion of a tattoo machine grip 100 is illustrated. The machine drive pin 900 engages contact disc 400, which in turn engages needle cartridge pin 201. In such an embodiment, the contact disc 400 may have an outer circumferential groove 420 (see FIG. 11) into which a disc mating portion 320 of the barrier 103 may correspondingly fit.

Figure 11:
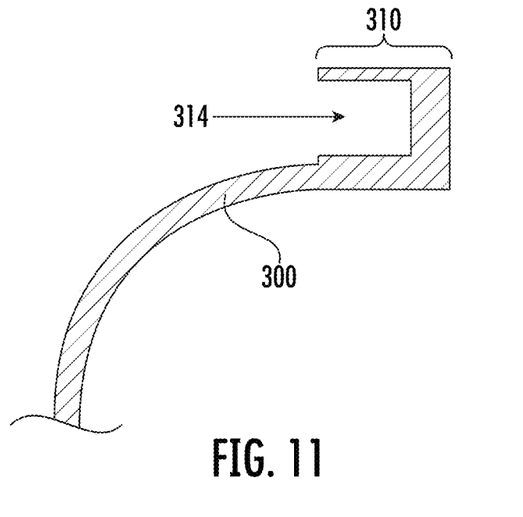
FIG. 11 illustrates a lateral cross sectional view of a resilient barrier bottom lip and groove in an embodiment of a grip.

FIG. 11 illustrates a closeup view of a cross section of a portion of the flexible portion 300 of the resilient barrier 103, including a barrier-grip mating portion 310 that includes a barrier outer circumferential groove 314. The barrier-grip mating portion 310 forms a seal against the inner wall of the grip housing 101, while flexible portion 300 allows rectilinear translation of the machine drive pin 900 against the resilient barrier 103 to the needle cartridge 200.

Figure 12:
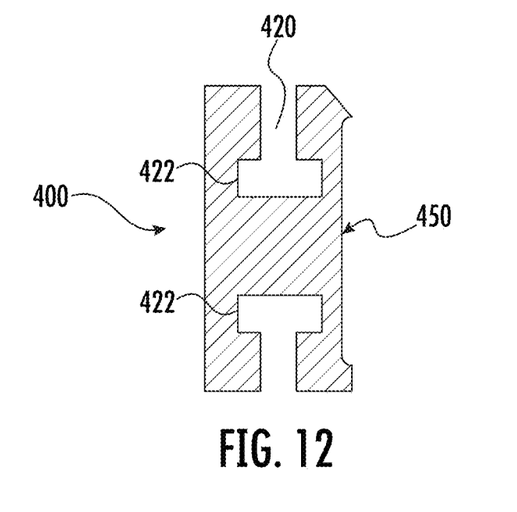
FIG. 12 illustrates a lateral cross sectional view of a contact disc in one embodiment of a grip.

Finally, FIG. 12 depicts an embodiment of a contact disc 400 showing disc mating portion groove 420 along its outer circumference, inner channel 422 within the mating portion groove 420, and concave alignment feature 450.

In light of the foregoing description, it should be recognized that embodiments in accordance with the present disclosure can be realized in numerous configurations contemplated to be within the scope and spirit of the claims. Additionally, the description above is intended by way of example only and is not intended to limit the present disclosure in any way, except as set forth in the claims.

In addition, though the disclosure has been described in reference to several examples optionally incorporating various features, the disclosure is not to be limited to that which is described or indicated as contemplated with respect to each variation of the disclosure. Various changes may be made to the disclosure described and equivalents (whether recited herein or not included for the sake of some brevity) may be substituted without departing from the true spirit and scope of the disclosure. In addition, where a range of values is provided, it is understood that every intervening value, between the upper and lower limit of that range and any other stated or intervening value in that stated range, is encompassed within the disclosure.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present disclosure is not to be limited to the examples provided and/or the subject specification, but rather only by the scope of claim language associated with this disclosure.

What is claimed is:

1. A tattoo machine grip apparatus, comprising:
   a grip housing having substantially radial symmetry about a central axis, a hollow interior, a cartridge receiving end, and a motor housing mating portion opposite the cartridge receiving end, the cartridge receiving end having a bore co-axial to the central axis and dimensioned to receive a needle cartridge;
   a threaded retaining ring that engages threads on the motor housing mating portion; and
   a resilient barrier within the hollow interior, positioned between the cartridge receiving end and the motor housing mating portion, wherein the resilient barrier isolates the cartridge receiving end from the motor housing mating portion.

2. The tattoo machine grip of claim 1, further comprising:
   a contact disc integral with the resilient barrier, the contact disc positioned co-axially to the central axis and configured to provide mechanical communication between a machine drive pin and a cartridge pin.

3. The tattoo machine grip of claim 2, wherein the resilient barrier has an outer circumference, the outer circumference co-axial to the central axis and positioned longitudinally distal to the contact disc, thereby defining a deformable concave surface.

4. The tattoo machine grip of claim 2, wherein the resilient barrier has an outer circumference, the outer circumference co-axial to the central axis and positioned concentric to the contact disc.

5. The tattoo machine grip of claim 2, wherein the contact disc has a circumferential groove dimensioned to receive an inner circumference of the resilient barrier.

6. The tattoo machine grip of claim 2, wherein the contact disc further comprises one or more alignment structures.

7. The tattoo machine grip of claim 2, wherein the contact disc has a machine face and a cartridge face, wherein the cartridge face of the contact disc has one or more cartridge alignment structures, and wherein the machine face of the contact disc has one or more machine alignment structures.

8. The tattoo machine grip of claim 7, wherein the one or more machine alignment structures and the one or more cartridge alignment structures are selected from the group consisting of concave, convex, stepped configurations, or a combination thereof.

9. The tattoo machine grip of claim 1, wherein the resilient barrier has an outer circumference, a center point, and one or more concentric undulations, wherein the outer circumference is co-axial to the central axis and mated to the hollow interior of the grip, the center point co-axial to the central axis, and the one or more concentric undulations existing between the outer circumference and the center point.

10. The tattoo machine grip of claim 1, further comprising:
    a toric gasket, the toric gasket positioned within the cartridge receiving end and co-axial to the central axis, wherein the toric gasket seals the cartridge receiving end when a needle cartridge is constrained therein.

11. The tattoo machine grip of claim 1, wherein the grip housing has an exterior antimicrobial surface.

12. A tattoo machine kit, comprising:
    a grip housing having a hollow interior substantially radial symmetry defining a central axis and having a cartridge receiving end and a motor housing mating portion distal to the cartridge receiving end, the cartridge receiving end having a bore co-axial to the central axis and dimensioned to receive a needle cartridge;

a threaded retaining ring that engages threads on the motor housing mating portion;

a resilient barrier within the hollow interior, positioned between the cartridge receiving end and the motor housing mating portion, wherein the resilient barrier isolates the cartridge receiving end from the motor housing mating portion; and a machine drive pin dimensioned to attach to a reciprocating machine configured to operatively mate with the motor housing mating portion, the machine drive pin further dimensioned to engage a contact disc integral with the resilient barrier.

13. The kit of claim 12, further comprising:

the needle cartridge dimensioned to engage the hollow interior at the cartridge receiving end, the needle cartridge having a needle coupled to a cartridge pin located within the needle cartridge, the cartridge pin dimensioned to engage the contact disc; and, the reciprocating machine dimensioned to engage a toric gasket on the interior side of the motor housing mating portion.

\* \* \* \* \*